United States Patent [19]
Itou et al.

[11] Patent Number: 5,096,944
[45] Date of Patent: Mar. 17, 1992

[54] PROCESS FOR PREPARING PARTICLES OF HIGH WATER-ABSORBENT RESIN

[75] Inventors: Tomiji Itou, Ogaki; Tetsuo Moriya, Takatsuki; Susumu Kondo, Kyoto, all of Japan

[73] Assignee: Nippon Gohsei Kagaku Kabushiki, Osaka, Japan

[21] Appl. No.: 515,136

[22] Filed: Apr. 26, 1990

[30] Foreign Application Priority Data

Apr. 26, 1989 [JP] Japan .................................. 1-106520

[51] Int. Cl.$^5$ ........................ C08J 3/20; C08K 5/09; C08F 6/00
[52] U.S. Cl. .................................. 523/351; 524/322; 524/916; 528/490; 528/491
[58] Field of Search ............... 524/322, 916; 528/491, 528/490; 523/351

[56] References Cited

U.S. PATENT DOCUMENTS

| | | | |
|---|---|---|---|
| 4,668,715 | 5/1987 | Phillips | 524/916 |
| 4,732,968 | 3/1988 | Obayashi et al. | 528/490 |

FOREIGN PATENT DOCUMENTS

| | | |
|---|---|---|
| 62-132936 | 6/1987 | Japan . |
| 62-254842 | 11/1987 | Japan . |
| 2162525A | 2/1986 | United Kingdom . |

Primary Examiner—Paul R. Michl
Assistant Examiner—Patrick Niland
Attorney, Agent, or Firm—Armstrong, Nikaido, Marmelstein, Kubovcik & Murray

[57] ABSTRACT

A process for preparing particles of a high water-absorbent resin which comprises mixing a powder of a high water-absorbent resin with a solution of a sorbitan surfactant having an HLB of 2.1 to 5.0 dissolved in an organic solvent, volatilizing the organic solvent from the mixture to give a resin powder with a content of the organic solvent of not more than 5% by weight, adding water to the mixture to adjust a water content in the resin powder to 25 to 60% by weight, adding an inorganic powder to the resin powder, and drying the resulting mixture. The particles of the high water-absorbent resin obtained according to the present invention are suitable for use of sanitary goods, water-retaining agents or soil conditioner in the fields of agriculture and horgiculture and other various uses.

3 Claims, No Drawings

PROCESS FOR PREPARING PARTICLES OF HIGH WATER-ABSORBENT RESIN

BACKGROUND OF THE INVENTION

The present invention relates to a process for preparing particles of a high water-absorbent resin, and more particularly to a process for preparing particles of a high water-absorbent resin which is suitably utilizable for sanitary goods such paper diapers, sanitary napkins, tampons and disposable dustclothes, water-retaining agents or soil conditioners in the fields of agriculture and horticulture, and other various uses of coagulation of sludge, prevention of dew condensation on building materials, dehydration of oil, and so on.

Water-absorbent resins have, hitherto, been used in the manufacture of paper diapers, sanitary napkins, tampons, disposable dustcloths and other sanitary goods, and as water-retaining agents or soil conditioners in the fields of agriculture and horticulture. They have been also used for the purpose of coagulation of sludge, prevention of dew condensation on building materials, dehydration of oil, and so on.

These known water-absorbent resins include crosslinked polyacrylic acid salts, hydrolyzates of crosslinked acrylic acid ester-vinyl acetate copolymers, crosslinked starch-acrylic acid salt graft copolymer, hydrolyzates of crosslinked starch-acrylonitrile graft copolymers, crosslinked polyvinyl alcohol grafted with maleic anhydride, crosslinked polyethylene oxide, and so on.

These high water-absorbent resin powders are prepared in a manner wherein a high water-absorbent polymer is prepared in reversed phase suspension polymerization, reversed phase emulsion polymerization, aqueous solution polymerization or a polymerization using an organic solvent, then the prepared polymer is dried as it is, further, when occasion demands, the dried one is pulverized.

The high water-absorbent resin powders prepared by the above-mentioned manners, however, are wide in particle size distribution and have quite a number of fine particles. When using the high water-absorbent resin particles in manufacture of the sanitary goods, in general, the particles are admixed with a pulverized pulp, are uniformly placed on the pulverized pulp layer, or are put between water-absorbing papers. Accordingly, if using the water-absorbent resin particles having quite a number of fine particles, not only it is troublesome to handle them, for instance, the bridging is easily caused during transportion or supply of the particles, but also the working surrounding is made remarkably bad or there is a case that the pollution or trouble of the apparatus is caused due to the dust. Further, the fine particles are got out of the surface or outer border of the sanitary good through the spaces between the pulp fibers.

As a process for preparing particles of a water-absorbent resin which improves the above-mentioned defects, there are processes described in Japanese Unexamined Patent Publication No. 61-97333 and No. 61-101536, wherein a mixture of a high water-absorbent resin powder and an inorganic powder is stirred by using a specific apparatus, and on the mixture is spraied an aqueous liquid such as water alone, an aqueous mixture of water and an organic solvent compatible with water, or an aqueous solution wherein a water-soluble hight molecular weight compound is dissolved in water or the aqueous mixture as mentioned above. The processes have, however, a defect that if a condition that the mixture is stirred at high speed by using a specific appatratus, on which the aqueous liquid is spraied in the sate of a fine droplet is not satisfactory, the blocking of the resin particles is caused partially.

Also, Japanese Unexamined Patent Publication No. 62-132936 discusses a process wherein an inorganic powder is added to a mixture of a high water-absorbent resin, water and a surfactant having an HLB (hydrophile-lypophile balance) of 6 to 12 in an inert solvent. However, according to the process, not only the use of the inert solvent is disadvantageous from the viewpoint of the recovery thereof but also since the solvent easily remains in the final particles, the particles are not sanitary. Moreover since the solvent easily catches fire, the particles are defective in safety.

It is an object of the present invention is to provide a process for preparing particles of a high water-absorbent resin which improves the above-mentioned defects.

This and other objects of the present invention will become apparent from the description hereinafter.

SUMMARY OF THE INVENTION

In accordance with the present invention, there is provided a process for preparing particles of a high water-absorbent resin which comprises:
  mixing a powder of a high water-absorbent resin with a solution of a sorbitan surfactant having an HLB of 2.1 to 5.0 dissolved in an organic solvent,
  volatilizing the organic solvent from the mixture to give a resin powder having a content of the organic solvent of not more than 5% by weight,
  adding water to the resin powder to adjust a water content in the resin powder to 35 to 60% by weight, adding an inorganic powder to the resin powder, and drying the resulting mixture.

DETAILED DESCRIPTION

According to the process for preparing the particles of the high water-absorbent resin of the present invention, a raw material, a powder of a high water-absorbent resin is mixed with a solution of a sorbitan surfactant having an HLB of 2.1 to 5 dissolved in an organic solvent, from which the organic solvent is volatilized to give a resin powder having a content of the organic solvent of not more than 5% by weight, then water is added to the resin powder to adjust a water content in the resin powder of 35 to 60% by weight, the thus obtained resin powder is admixed with an inorganic powder, and the resulting mixture is dried to give particles of the high water-absorbent resin.

The high water-absorbent resins used in the present invention are not particularly limited and known water-absorbent resins can be used without any limitation. Examples of the high water-absorbent resins are, for instance, crosslinked polyacrylic acid salts, hydrolyzates of crosslinked acrylic acid ester-vinyl acetate copolymers, crosslinked starch-acrylic acid salt graft copolymer, hydrolyzates of crosslinked starch-acrylonitrile graft copolymer, crosslinked polyvinyl alcohol grafted with maleic anhydride, crosslinked polyethylene oxide, and the like. Preferred among the high water-absorbent resins are the crosslinked polyacrylic acid salts, because the polymers are excellent in physical properties such as rate of water absorption.

These high water-absorbent resin powders are prepared, in general, by conducting a reversed phase suspension polymerization, reversed phase emulsion polymerization, aqueous solution polymerization or polymerization using an organic solvent to synthesize the high water-absorbent resin, and bring them, further pulvelizing the dried one when occasion demands.

Typical examples of the preparation methods of the high water-absorbent resin powder are as mentioned below.

(I) A method wherein an aqueous solution of an α,β-unsaturated carboxylic acid and its salt with an alkali metal is suspended in a solvent, a petroleum hydrocarbon containing a fatty acid ester of sucrose in the presence or absence of a crosslinking agent and the suspension is polymerized by using a radical polymerization initiator (II) A method wherein an aqueous solution of acrylic acid and its alkali salt is suspended in a solvent, an alicyclic or aliphatic hydrocarbon containing a surfactant with an HLB of 8 to 12, and the suspension is polymerized by using a water-soluble radical polymerization initiator (III) A method wherein an aqueous solution of monomers to be polymerized is suspended in a hydrophobic liquid inactive to polymerization and the suspension is polymerized by using a water-soluble radical polymerization initiator, using as a protective colloid, a reaction product obtained by grafting an olefin polymer having a molecular weight of 750 to 1000 with 1 to 20 % by weight of an α,β-unsaturated polyvalent carboxylic acid or its anhydride, or a product obtained by oxydizing an olefin polymer so as to finally have an acid value of 10 to 100

(IV) A method wherein an aqueous solution of a water-soluble ethylenically unsaturated monomer having a monomer concentration of 40% by weight to a saturation concentration is dispersed or suspended in a hydrocarbon or a halogenated aromatic hydrocarbon, and the dispersion or suspension is polymerized by using a presulfate as a polymerization initiator, using as a protective colloid a cellulose ester or cellulose ether assuming oil-solubility at the polymerization temperature (V) A method wherein a composition comprising (A) at least one of starch and cellulose, (B) at least one of a water-soluble monomer having addition-polymerizable double bond and a monomer convertible to a water-soluble monomer by hydrolysis, and (C) a crosslinking agent as essential components is polymerized and, if necessary, the polymerization product is hydrolyzed (VI) A method wherein a polymerization initiator is added to a warm aqueous solution containing potassium acrylate and a water-miscible or water-soluble divinyl compound and having a concentration of the monomrs of 55 to 80% by weight, and the mixture is polymerized without heating the polymerization system, while evaporating water The preparation method of the high water-absorbent resin powder used in the present invention is not limited to the above-mentioned methods (I) to (VI) and the resin powder may be prepared in any manner.

Also, in the present invention, the high water-absorbent resin powder whose surface is crosslinked by using a crosslinking agent such as an epoxy compound having the formula:

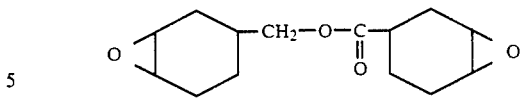

a condensation product of a long-chain dibasic acid and epichlorohydrin, or a reaction product of bisphenol A and epichlorohydrin may be used. The high water-absorbent resin powder whose surface is crosslinked is increased in rate of water absorption and dispersibility of water. In such a case, it is preferable that the amount of the crosslinking agent is from 0.0005 to 3 parts by weight, more preferably from 0.01 to 1 part by weight, based on 100 parts by weight of the high water-absorbent resin powder which is the raw material. If the amount of the crosslinking agent is more than 3 parts by weight, it tends to lower the water absorbency thereof.

The particle size and shape of the raw material, the high water-absorbent resin powder are not particularly limited. Generally, a particle size of the powder of 110 to 130 μm is preferred.

The high water-absorbent resin powder is mixed with the solution of the surfactant in the organic solvent.

In the present invention, as the surfactant, a sorbitan surfactant is used from the viewpoint that the high water-absorbent resin particles having a desired particle size distribution can be easily obtained. Among the sorbitan surfactants, in the present invention, a sorbitan surfactant having an HLB (hydrophile-lyophile balance) of 2.1 to 5.0, preferably from 3.3 to 4.7, more preferably from 3.7 to 4.7 is used. When the HLB of the sorbitan surfactant is less than 2.1, it tends to lower the rate of water absorption of the final water-absorbent resin particles. On the other hand, when the HLB is more than 5.0, it is impossible to uniformly mix the high water-absorbent resin powder with water when adding water to the resin powder with the surfactant, due to the small hydrophobic property of the surfactant.

Examples of the sorbitan surfactants are, for instance, sorbitan monostearate, sorbitan distearate, sorbitan monooleate, sorbitan dioleate, sorbitan trioleate, sorbitan sesquioleate, and the like. Among them, sorbitan monostearate, sorbitan monooleate, sorbitan trioleate and sorbitan sesquioleate are preferable from the viewpoint that it is difficult to generate undissolved lumps of the final high water-absorbent resin particles when contacting the resin particles with a liquid, and the rate of water absorption of the resin particles is made suitable.

The amount of the surfactant is from 50 to 5000 ppm, preferably from 100 to 1500 ppm, more preferably from 150 to 1000 ppm, based on the high water-absorbent resin powder which is the raw material. When the amount of the surfactant is less than 50 ppm, there is a tendency that it is difficult to uniformly admix the high water-absorbent resin powder with water. On the other hand, when the amount of the surfactant is more than 5000 ppm, there is a tendency that the rate of water absorption is too slow.

The high-absorbent resin powder may contain water so long as the water content is not more than 30% by weight, in case of mixing the high water-absorbent resin powder with the surfactant.

The surfactant is dissolved in the organic solvent. Examples of the organic solvents are, for instance, cyclohexane, n-hexane, benzene, toluene, and the like. The amount of the organic solvent varies depending on the kinds of the high water-absorbent resin powder and the surfactant. Generally, the amount of the organic solvent is from 10 to 40 parts by weight, preferably from 15 to 30 parts by weight, based on 100 parts by weight of the high water-absorbent resin powder which is the raw material.

In the present invention, after mixing the high water-absorbent resin powder with the solution of the sorbitan surfactant dissolved in the organic solvent and before adding water to the resin powder, the organic solvent is volatilized from the high water-absorbent resin powder in a usual manner to lower the organic solvent content of the resin powder as low as possible. It is preferable that the volatilization of the organic solvent is conducted under an atmosphere of nitrogen. Further, it is preferable that after volatilizing the organic solvent, a temperature of the reaction system is elevated to 50° to 80° C. and is maintained at the temperature for 0.3 to 2 hours, in case of crosslinking the high water-absorbent resin powder surface. The volatilization of the organic solvent is conducted to adjust the content of the organic solvent remaining in the water-absorbent resin powder to not more than 5% by weight, preferably not more than 1% by weight, more preferably not more than 0.5% by weight. When the organic solvent content is more than 5% by weight, the strength of the final resin particles becomes poor.

After mixing the water-absorbent resin powder with the surfactant in the organic solvent then volatilizing the organic solvent therefrom to adjust the content of the organic solvent remaining in the resin powder to not more than 5% by weight, water is added to the resulting high water-absorbent resin powder at a temperature of room temperature to 80° C. In the present invention, any water is used without any limitation. It is preferable to use pure water. Water is added to the high water-absorbent resin powder with stirring to adjust the water content of the resin powder to 35 to 60% by weight, preferably from 35 to 50% by weight, more preferably from 40 to 45% by weight. When the water content is less than 35% by weight, it is difficult to prepare the particles of the high water-absorbent resin. On the other hand, when the water content is more than 60% by weight, the final particles are too hard to lower the rate of water absorption.

The high water-absorbent resin powder to which water is added is in the loosely aggregated state. To obtain the final particles having the suitable strength and the high rate of water absorption, the inorganic powder is added to the water-absorbent resin powder. The inorganic powder is admixed in the state of a dried powder or a slurry, an aqueous dispersion, with the high water-absorbent resin powder. The mixing method is not particularly limited. It is particularly preferable to add the organic powder to the high water-absorbent resin powder little by little.

Examples of the inorganic powders are, for instance, silicon dioxide powder, calcium carbonate powder, aluminum oxide powder, titanium dioxide powder, and the like. Among them, the silicon dioxide powder is preferably used.

It is preferable that an average particle size of the inorganic powder is from 0.1 to 20 μm, more preferably from 1 to 10 μm.

The amount of the inorganic powder is from 0.005 to 5 parts by weight, preferably from 0.05 to 3 parts by weight, more preferably from 0.1 to 2 parts by weight, based on 100 parts by weight of the high water-absorbent resin powder which is the raw material. When the amount of the inorganic powder is less than 0.005 part by weight, the final particles are poor in mechanical strength and slow in rate of water absorption. On the other hand, when the amount of the inorganic powder is more than 5 parts by weight, the final particles are too large, and are too small in rate of water absorption since the particles are great in mechanical strength so they are too hard.

After admixing the high water-absorbent resin powder with the inorganic powder, the mixture is dried in a usual manner to give the final particles of the high water-absorbent resin. It is preferable that the mixture is dried at a temperature of 50° to 80° C. for 1 to 2 hours in the atmosphere then is dried at a temperature of 50° to 90° C. for 1 to 2 hours in vacuo.

The particle size and shape of the final particles are not particularly limited. Generally, a particle size of about 12 to 100 mesh is preferred.

The thus obtained particles of the high water-absorbent resin according to the present invention are uniform in density, and dissolved lumps thereof are not generated. Also, the obtained particles have scarcely the solvent, so are sanitary and safe. Further, the particles have the preferable strength, and have useful particle size for, e.g., the sanitary goods, such as about 12 to 100 mesh. Moreover, the particles are remarkably improved in rate of the water absorption in comparison with the conventional particles.

The present invention is more specifically described and explained by means of the following Examples wherein all per cents and parts are by weight unless otherwise noted. It is to be understood that the present invention is not limited to the Examples, and various changes and modifications may be made in the invention without departing from the spirit and scope thereof.

Reference Example 1

[Preparation of fine particles of sodium polyacrylate by reversed phase suspension polymerization]

A 500 ml beaker was charged with 100 g of acrylic acid, and it was neutralized with 157 g of a 25.9% aqueous solution of sodium hydroxide under cooling to give an aqueous solution of partially neutralized acrylic acid. A 300 ml dropping funnel was charged with the obtained aqueous solution of partially neutralized acrylic acid and it was bubbled for 30 minutes by using nitrogen gas. Then, to the aqueous solution were added 3 ml of a 7% aqueous solution of APS (ammonium persulfate) and 1 ml of a 1% aqueous solution of N,N'-methylene-bis-(acrylamide), and the mixture was thoroughly mixed to give a mixed aqueous solution of the aqueous solution of the partially neutralized acrylic acid, APS and N,N'-methylenebis(acrylamide).

Separately, a 2 l separable flask was charged with 760 ml of cyclohexane, in which 4 g of sorbitan monostearate having an HLB of 4.7 was dissolved. Then the cyclohexane solution of sorbitan monostearate was bubbled at 25° C. for 30 minutes by using nitrogen gas (total volume of nitrogen gas: 10 l) to remove dissolved oxygen in the solution and air in the space of the flask from the flask. The internal temperature of the flask was raised to 72° C., and the mixed aqueous solution of the aqueous solution of the partially neutralized acrylic acid, APS and N,N'-methylenebis(acrylamide) obtained as above was added dropwise over 1 hour to the separable flask with stirring to polymerize. Further the polymerization was continued at 72° C. over 1 hour to complete the polymerization. Then, the polymerization mixture was cooled down to 35° C. and it was filtered under reduced pressure by using a Nutsche funnel, a filtering flask and a filter paper. A 500 ml kneader was charged with the obtained filtered residue and it was dried at 70° C. for 3 hours under reduced pressure (about 50 mmHg) to give a high water-absorbent resin powder, which was a crosslinked polyacrylic acid salt having a water content of 25%. The high water-absorbent resin powder was in the form of pearly particles and had an average particle size of 110 μm.

The flask was charged with the obtained high water-absorbent resin powder and 1 l of cyclohexane, and the mixture was stirred at 30° C. for 30 minutes and was filtered under reduced pressure by using a Neutsche funnel, a filtering flask and a filter paper. The procedure of the addition of cyclohexane to the resin powder, then the stirring of the mixture and finally the filtration was repeated 5 times to completely remove sorbitan monostearat from the obtained resin powder.

Reference Example 2

[Preparation of sodium polyacrylate by aqueous solution polymerizaton in static state]

The same mixed aqueous solution of the aqueous solution of partially neutralized acrylic acid, ASP and N,N'-methylenebis(acrylamide) as obtained in Reference Example 1 was obtained in the same manner as in Reference Example 1.

Separately, an open side (upper side) of a flat bottom stainless steel vat (200 mm × 150 mm) was completely sealed with a polyester sheet, and a hole having a diameter of about 10 mmφ was made on the center of the sheet. A rubber hosepipe was attached to the vat through the hole, and nitrogen gas was supplied to the vat via the hosepipe to thoroughly substitute nitrogen gas for air in the space of the vat.

The mixed aqueous solution obtained as above was poured into the vat, then the vat was dipped in a warm bath having a temperature of 60° C., and the polymerization was conducted. After about 10 minutes, the internal temperature of the vat reached to the maximum temperature, 105° C. The vat was dipped in a warm bath having a temperature of 60° C. over 2 hours, then was cooled down to a temperature of 20° C. to give a sheet of a crosslinked polyacrylic acid salt. The obtained sheet was taken out from the vat, and was cut off with scissors to give chips. The chips were dried in a vacuum drier having a temperature of 90° C. for 30 minutes. The dried chips were pulverized by using a pulverizer and a powder having a particle size of 70 to 200 mesh was separated from the pulverized chips.

EXAMPLE 1

A 1 l kneader was charged with 200 g of the powder of the high water-absorbent resin having the water content of 25%, obtained in Reference Example 1, and a solution composed of 0.1 g of sorbitan monostearate having an HLB of 4.7, 0.04 g of an epoxy compound which is a crosslinking agent having the formula:

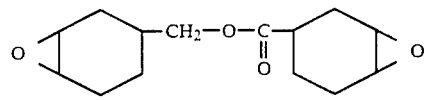

and 60 g of cyclohexane was admixed with the resin powder in the kneader at room temperature. Then, cyclohexane was removed from the mixture at room temperature by satisfactorily passing nitrogen gas through the kneader to give the high water-absorbent resin powder having the cyclohexane content of not more than 0.5%. (The solvent content was measured as mentioned below.)

After the oder of cyclohexane was lost, the internal temperature of the kneader was elevated to 70° C. and was maintained at 70° C. for 1 hour. After 1 hour, 30 g of pure water was added to the kneader. The water content of the obtained high water-absorbent resin powder was 40%, and blocks (undissoved lumps of the powder) were not generated. (The water content was measured as mentioned below.)

After stirring the aqueous mixture for 30 minutes, to which 1.0 g of fine particles of silica (commercially available from Nippon Silica Kabushiki Kaisha under a trade mark "Nipsil Lp") was added at 70° C. over about 30 minutes little by little.

The mixture was dried at 70° C. for 1.5 hours in the atmosphere, opening the lid of the kneader, then was dried at 90° C. for 1.5 hours in a vacuum drier to give particles of the high water-absorbent resin.

The obtained particles were separated by using a 12-mesh wire net and a 100-mesh wire net. As a result, it was confirmed that useful particles having a particle size of 12 mesh to 100 mesh account for 93% of the total of the obtained particles, that is, the process for preparing particles of the present invention was excellent in granulation property.

As to the high water-absorbent resin powder, the water content and the content of the remaining solvent were measured as mentioned below. As to the resin particles having a particle size of 12 to 100 mesh, the rate of synthetic urine absorption, the absorption ratio, and the urine diffusion were measured.

The results are shown in Table 1 with the particle size distribution of the final particles.

[Water content (%)]

About 10 g [(S)g] of a high water-absorbent resin powder to be measured the water content was placed on a glass evaporating dish having a weight of (A)g and a diameter of 100 mmφ, and it was dried at 90° C. for 3 hours in a vacuum drier. After drying, the weight [(B)g] of the resin powder with the dish was weighed. The water content was calculated according to the following equation.

$$\text{Water content (\%)} = \frac{S - (B - A)}{B - A} \times 100$$

[Content of remaining solvent (%)]

About 1 g of a high water-absorbent resin powder to be measured the content of the solvent remaining therein was added to a flask charged with methanol having a weight 1000 times the weight of the resin powder, the flask was allowed to stand for 1 hour while it was lightly shaked at intervals. The content of the solvent remaining in the high water-absorbent resin powder was measured according to a gas chromatography of the supernatant liquid in the flask.

[Rate of synthetic urine absorption (g/g·3 minutes)]

As to the final particles having a particle size of 12 to 100 mesh, the rate of synthetic urine absorption was measured according to a tea bag method.

[Absorption ratio concerning physiological saline water or deionized water (times)]

To a 500 ml beaker were added 0.2 g of the dried final resin particles and 60 g of physiological saline water (0.9% aqueous solution of sodium chloride) or 200 g of deionized water. After the mixture was lightly stirred with a glass bar, it was allowed to stand for 1 hour at room temperature, and the particles were filtered off through a 325-mesh wire net. The weight of the gel remaining on the net was measured and the absorption ratio was calcultaed according to the following equation.

$$\text{Absorption ratio} = \frac{[\text{Weight of the gel remaining on the net (g)}] - [\text{Weight of the dried final particles (0.2 g)}]}{[\text{Weight of the dried final particles (0.2 g)}]}$$

[Urine diffusion (mm)]

Five grams of the final resin particles were uniformly scattered on the center of a sheet of a fleecy pulp (length: 120 mm, width: 280 mm, thickness: 5 mm) in an area of 100 mm × 240 mm, on which the same sheet as above was placed, and the surface was lightly pressed to give a diaper for testing.

A dropping funnel was attached to the center of the diaper for testing and 200 ml of the synthetic urine was poured into the diaper. After 30 minutes the upper fleecy pulp sheet was removed, the length [(diffusion length (mm)] of the area wherein the swollen resin particles with the synthetic urine were placed was measured. The urine diffusion is an important physical property, as to goods having an absorption band such as diapers, because the longer the diffusion length, the more excellent the absorption of the high water-absorbent resin particles.

EXAMPLES 2 to 4

Particles of a high water-absorbent resin were prepared in the same manner as in Example 1 except that a high water-absorbent resin powder which was a raw material, a surfactant, and an inorganic powder shown in Table 1 were used.

As to the particles, the physical properties were measured in the same manner as in Example 1.

The results are shown in Table 1 with the particle size distribution.

Comparative Example 1

The procedure of Example 1 was repeated except that a surfactant was not used to give particles of a high water-absorbent resin.

As to the particles, the physical properties were measured in the same manner as in Example 1.

The results are shown in Table 1 with the particle size distribution.

Comparative Example 2

The procedure of Example 1 was repeated except that cyclohexane was not removed from the polymerization system to give particles of a high water-absorbent resin.

As to the particles, the physical properties were measured in the same manner as in Example 1.

The results are shown in Table 1 with the particle size distribution.

TABLE 1

| Ex. No. | Powder of the high water-absorbent resin (raw material) Kind | Amount (g) | Surfactant Kind | Percentage to the raw material (%) |
|---|---|---|---|---|
| Ex. 1 | Resin powder in Ref. Ex. 1 | 200 | Sorbitan monostearate HLB: 4.7 | 0.05 |
| Ex. 2 | Resin powder in Ref. Ex. 2 | 200 | Sorbitan sesquioleate HLB: 3.7 | 0.08 |
| Ex. 3 | Resin powder in Ref. Ex. 1 | 200 | Sorbitan monostearate HLB: 4.7 | 0.05 |
| Ex. 4 | Resin powder in Ref. Ex. 1 | 200 | Sorbitan monostearate HLB: 4.7 | 0.05 |
| Com. Ex. 1 | Resin powder in Ref. Ex. 1 | 200 | — | — |
| Com. Ex. 2 | Resin powder in Ref. Ex. 1 | 200 | Sorbitan monostearate HLB: 4.7 | 0.05 |

| | Content of the solvent remaining in the powder | Water content of the powder | Inorganic powder Kind | Amount (part)*[1] |
|---|---|---|---|---|
| Ex. 1 | Not more than 5% | 40% | Nipsil Lp | 0.5 |
| Ex. 2 | Not more than 5% | 40% | Alumina 160 SG*[2] | 1.0 |
| Ex. 3 | Not more than 5% | 35% | Nipsil Lp | 0.5 |
| Ex. 4 | Not more than 5% | 55% | Nipsil Lp | 0.5 |
| Com. Ex. 1 | Not more than 5% | 40% | Nipsil Lp | 0.5 |
| Com. Ex. 2 | 10% | 40% | Nipsil Lp | 0.5 |

| | Particle size distribution of the final particles | | | Physical properties of the final particles Rate of synthetic urine absorption (g/g · 3 minutes) |
|---|---|---|---|---|
| | Not less than 12 mesh (%) | From 12 to 100 mesh (%) | Not more than 100 mesh (%) | |
| Ex. 1 | 6 | 91 | 3 | 30 |
| Ex. 2 | 5 | 93 | 2 | 30 |
| Ex. 3 | 3 | 72 | 25 | 30 |
| Ex. 4 | 18 | 80 | 2 | 27 |
| Com. Ex. 1 | 46 | 52 | 2 | 20 |
| Com. Ex. 2 | 60 | 39 | 1 | 20 |

| | Physical properties of the final particles | | |
|---|---|---|---|
| | Absorption ratio (times) | | |
| | Deionized water | Saline | Urine diffusion (mm) |
| Ex. 1 | 350 | 50 | 180 |
| Ex. 2 | 380 | 53 | 200 |
| Ex. 3 | 350 | 50 | 170 |
| Ex. 4 | 350 | 50 | 200 |
| Com. Ex. 1 | 280 | 46 | 150 |
| Com. Ex. 2 | 300 | 47 | 150 |

(Notes)
*[1] part based on 100 parts of the powder of the high water-absorbent resin (raw material)
*[2] Aluminum oxide powder commercially available form Showa Keikinzoku Kabushiki Kaisha (Trade mark)

The results of Table 1 show that as to the particles of the high water-absorbent resin obtained in Examples 1-4, particles having a useful particle size, 12 to 100 mesh account for not less than 72% of the total of the obtained final particles, and they are more excellent in granulation property than those obtained in Comparative Examples 1 and 2. Moreover, the final particles obtained in Examples 1 to 4 are remarkably superior in rate of synthetic urine absorption, absorption ratio concerning deionized water, absorption ratio concerning physiological saline water and urine diffusion to the final particles obtained in Comparative Examples 1 and 2.

According to the process of the present invention, the particles of the high water-absorbent resin suitable for various use such as agents for improving water absorption used in sanitary goods, e.g., diapers, sanitary napkins or tampons, water-retaining agents or soil conditioners in the fields of agriculture and horticulture can be obtained. Because, according to the process of the invention, the final particles are uniform in density, are sanitary and safe to the human bodies since the particles have scarcely the solvent and are suitable in strength, and undissolved lumps of the particles are not generated. Moreover, the most of the obtained final particles have useful particles sizes, and they are remarkably improved in rate of water absorption compared to the particles obtained according to the conventional method.

In addition to the ingredients used in the Examples, other ingredients can be used in the Examples as set forth in the specification to obtain substantially the same results.

What we claim is:

1. A process for preparing particles of a high water-absorbent resin which comprises:
    mixing a powder of a high water-absorbent resin with a solution of a sorbitan surfactant having an HLB of 2.1 to 5.0 dissolved in an organic solvent,
    volatilizing the organic solvent from the mixture to give a resin powder with a content of the organic solvent of not more than 5% by weight,
    adding water to the mixture to a water content in the resin powder of 35 to 60% by weight,
    adding an inorganic powder to the resin powder, and drying the resulting mixture.

2. The process of claim 1, wherein the powder of the high water-absorbent resin is a powder of a crosslinked polyacrylic acid salt.

3. The process of claim 1, wherein the amount of the organic solvent is from 10 to 40 parts by weight per 100 parts by weight of the powder of the high water-absorbent resin.

* * * * *